United States Patent [19]

Firth

[11] 4,418,223

[45] Nov. 29, 1983

[54] PREPARATION OF 2,4,6-TRIALKYLPHENOLS

[75] Inventor: Bruce E. Firth, Elk Grove, Ill.

[73] Assignee: UOP Inc., Des Plaines, Ill.

[21] Appl. No.: 362,774

[22] Filed: Mar. 29, 1982

[51] Int. Cl.³ .................. C07C 37/14; C07C 39/06
[52] U.S. Cl. ................................. 568/794; 568/781
[58] Field of Search .................. 568/781, 794, 789

[56] References Cited

U.S. PATENT DOCUMENTS

| | | | |
|---|---|---|---|
| 2,684,389 | 7/1954 | Offutt | 260/624 |
| 3,437,603 | 4/1969 | Hilfman | 252/453 |
| 3,470,257 | 9/1969 | Sparks | 260/613 |
| 3,631,120 | 12/1971 | Eberly, Jr. et al. | 260/671 |
| 3,683,030 | 8/1972 | Sparks | 260/613 D |
| 3,992,455 | 11/1976 | Leston | 568/781 |
| 4,166,191 | 8/1979 | Ueoka et al. | 568/789 |
| 4,275,248 | 6/1981 | Firth | 568/781 |

Primary Examiner—Werren B. Lone
Attorney, Agent, or Firm—James R. Hoatson, Jr.; Eugene I. Snyder; William H. Page, II

[57] ABSTRACT

Phenols may be alkylated with monosubstituted or alpha, beta-disubstituted olefins over a silica alumina composite to afford 2,4,6-tri-sec-alkylphenols in high yields. The alkylation catalyst shows high activity and high selectivity to the 2,4,6-trialkylated product while minimizing oligomerization of the olefin. Composites containing from about 40 to about 60% silica, the remainder being alumina, are especially valuable.

6 Claims, No Drawings

PREPARATION OF 2,4,6-TRIALKYLPHENOLS

BACKGROUND OF THE INVENTION

Alkylated phenols are widely employed as antioxidants in a broad spectrum of products, spanning the gamut from foods to fuel oils. Among such alkylated phenols it has been found that 2,4,6-trialkylphenols are especially effective antioxidants in fuel oils, and in particular 2,4,6-triisopropylphenol is an excellent stabilizer for a broad range of fuel oils, including gasoline.

A characteristic displayed by alkylation processes used in the preparation of, for example, 2,4,6-triisopropylphenol from propylene and phenol is that 2,6-diisopropylphenol in particular, and 2,6-dialkylphenols in general, are by-products which are generally much more difficult to alkylate in comparison to other positional isomers. Since the effectiveness of the 2,4,6-trialkylphenols as antioxidants generally surpasses that of the 2,6-dialkylated phenol it is very desirable that any preparative method maximize the formation of 2,4,6-trialkylphenol. In this context it must be emphasized that even a relatively small improvement in the yield of the 2,4,6-trialkylphenol represents a substantial advance in the art and is of commercially great importance.

Silica-alumina combinations have been used as a catalyst in the alkylation of phenols with olefins. U.S. Pat. No. 2,684,389 teaches the use of a silica-alumina composite which is predominantly silica to alkylate cresol with isobutylene at a temperature less than about 180° C. In U.S. Pat. No. 3,631,120 the patentee uses ammonium ion exchanged, calcined crystalline zeolite with a silica-alumina ratio between 4 and 4.9 as an alkylation catalyst. A composite of silica-alumina doped with an alkaline earth metal is disclosed as a catalyst in alkylation with isobutylene in U.S. Pat. No. 3,470,257, and a similar composite doped with a nitrogen-containing Lewis base is similarly utilized by the same patentee in U.S. Pat. No. 3,683,030. A process for preparing high purity p-tert-butylphenol using isobutylene oligomers as an alkylation agent with a silica-alumina catalyst in the presence of water is taught in U.S. Pat. No. 4,166,191.

This application discloses a method of trialkylating phenol with an olefin using a silica-alumina composite as a catalyst. More specifically, the invention is a method of trialkylating phenol with an olefin over a silica-alumina composite containing 40–60% silica at a temperature in the range from about 150° to about 300° C. In a still more specific embodiment the olefin is propylene.

An advantage of the method described herein is that the alkylating catalyst shows high activity while displaying high selectivity for the products of interest. In particular, the method of this invention affords improved yields of 2,4,6-trialkylphenols. More specifically, the method of this invention gives a higher yield of 2,4,6-triisopropylphenol relative to prior art methods involving heterogeneous catalysis. Another advantage of this invention is that alkylation with alpha-monosubstituted and alpha, beta-disubstituted olefins occur under conditions where there is little attending oligomerization.

DESCRIPTION OF THE INVENTION

The invention described within is a method of preparing 2,4,6-tri-sec-alkylphenols by reacting phenol with a monosubstituted or alpha, beta-disubstituted olefin at a temperature from about 150° to about 300° C. in the presence of a catalyst which is a composite consisting essentially of silica and alumina containing from about 40 to about 60% silica and from about 60 to about 40% alumina, and recovering the 2,4,6-tri-sec-alkylphenol. When alkylation is performed according to the teachings within, 2,4,6-tri-sec-alkylphenols are formed with good conversion and selectivity, and with relatively little oligomerization of the olefin.

The olefins which may be used in the practice of this invention are monosubstituted olefins and alpha, beta-disubstituted olefins containing up to about 10 carbon atoms. That is to say, the olefins are those which introduce a secondary alkyl group upon alkylation of phenol. These olefins may be represented by the formula $R_1CH=CHR_2$. Monosubstituted olefins are those where $R_1$ is a saturated alkyl group and $R_2$ is hydrogen. Alpha, beta-disubstituted olefins are those where both $R_1$ and $R_2$ are saturated alkyl groups. It is preferred that the olefin contain up to about 10 carbon atoms, which is to say that the total carbon content of $R_1$ and $R_2$ may be up to about 8. Propylene is an especially preferred olefin, and examples of other suitable olefins include 1-butene, 2-butene, 1-pentene, 2-pentene, 3-methyl-1-butene, 1-hexene, 2-hexene, 3-hexene, 3-methyl-1-pentene, 4-methyl-1-pentene, 4-methyl-2-pentene, and the isomeric heptenes, octenes, nonenes, and decenes corresponding to the prior description of suitable olefins.

The ratio of olefin to phenol used in the practice of this invention is from about 3.5:1 to about 10:1, with the range from about 4:1 to about 7:1 being more usually employed. Generally the pressure is that autogenous to the reactants employed although higher pressures may be used by introducing a suitable inert gas.

The alkylation catalyst is a composite consisting essentially of silica and alumina, with the composites of greatest interest being generally synthetic silica-alumina mixtures. The composites used should contain from about 40 to about 60% silica and from about 60 to about 40% alumina, with that containing approximately equal amounts of silica and alumina being somewhat advantageous. Although the apparent bulk density (ABD) and surface area of the composite is not critical to the success of this invention, a preferred embodiment utilizes a composite with an ABD from about 0.45 to about 0.65 and a surface area from about 200 to about 350 m²/g.

When the reaction is run at a temperature from about 150° to about 300° C., the product 2,4,6-tri-sec-alkylphenol is formed reasonably rapidly without excessive oligomerization of the olefin, especially propylene. The narrower temperature range from about 200° to about 250° C. has been found especially desirable.

The alkylation method described herein may be practiced either in the batch mode or a continuous mode, with continuous alkylation being generally preferred. As an example of a batch preparation, phenol and a silica-alumina composite of appropriate composition may be mixed in, for example, an autoclave. The amount of composite may be from about 1 to greater than 100 wt. % based on phenol. Olefin is then introduced at a mole ratio from about 3.5:1 to about 10:1 based on phenol. The reaction mixture is then brought to temperature in the range from about 150° to about 300° C., mixed, and reaction is permitted to continue for a time up to about 10 hours. The composite is then removed from the cooled mixture by suitable means, as by filtration, and the desired 2,4,6-tri-sec-alkylphenol is recovered, as for example by distillation.

When the reaction is conducted in a continuous fashion suitable methods include fixed bed, expanded bed, fluidized bed, and so forth. Using a fixed bed as an example, a mixture of olefin and phenol in a mole ratio from about 3.5:1 to about 10:1 is passed over a fixed bed of a silica-alumina composite at a temperature from about 150° to about 300° C. The liquid hourly space velocity used will depend on, inter alia, the olefin used, its mole ratio to phenol, and reaction temperature, and typically may be in the range from about 0.25 to about 5.0. Effluent is collected and the desired 2,4,6-tri-sec-alkylphenol may be separated by suitable means, as for example by distillation.

The following examples are illustrative of this invention and are not intended to limit the invention thereto.

EXAMPLE 1

The following alkylations were performed in a 300 ml rocking autoclave under autogeneous pressure. Propylene was added to the sealed autoclave containing catalyst and phenol, after which the mixture was maintained at reaction temperature for the indicated times. The cooled mixture was filtered and the filtrate analyzed by gas-liquid phase chromatography (glpc). Results are shown in Table 1. In all cases the silica-alumina catalyst was prepared as described in U.S. Pat. No. 3,437,603.

TABLE 1

| | Autoclave Isopropylation of Phenol | | | | | | | |
|---|---|---|---|---|---|---|---|---|
| | Catalyst | | Phenol | Olefin:Phenol[c] | T (t)[a] | | Wt. % other | Products[b] | other |
| Run No. | Si:Al | Wt (g) | (g) | (molar ratio) | °C. (hr) | 2,6- | dialkylates | 2,4,6- | trialkylates |
| 1 | 3:1 | 25 | 30 | 4 | 175(5) | 2.6 | 4.4 | 73.7 | 20.8 |
| 2 | 12:88 | 25 | 30 | 5 | 175(5) | 5.7 | 10.1 | 66.5 | 17.0 |
| 3 | 37:63 | 25 | 30 | 4 | 150(2) | 1.8 | 9.1 | 71.2 | 17.4 |
| 4 | 1:1 | 5 | 20 | 5 | 200(2) | 4.0 | 3.6 | 79.1 | 13.3 |

[a]Reaction temperature (T) and time (t).
[b]2,6- = 2,6-diisopropylphenol
2,4,6- = 2,4,6-triisopropylphenol
other dialkylates are the 2,4-, 2,5-, and 3,5-diisopropylphenol
other trialkylates include all material eluting from the glpc column after 2,4,6-triisopropylphenol.
[c]Other experiments showed little difference between using a 4:1 or 5:1 ratio.

As the table shows, product distribution is surprisingly sensitive to the silica-alumina composition. Even more unexpectedly, the optimum for 2,4,6-triisopropylphenol formation is about 1:1 silica:alumina, with a substantial decrease on either side of the optimum.

EXAMPLE 2

Continuous alkylations were performed using a fixed bed of 50 cc catalyst. No major differences were observed between upflow and downflow operation, and the data below were obtained from a downflow mode. It was also found that pressure changes in the range 500–1500 psig had little effect on the results. In the accompanying table the propylene to phenol molar ratio was 5.

TABLE 2

| | | | | | | Continuous Isopropylation of Phenol | | | | |
|---|---|---|---|---|---|---|---|---|---|---|
| | | | | | | | Product Distributions (Wt. %)[b] | | | |
| Run | Catalyst[a] | Pressure (psig) | Temp. (°C.) | LHSV | Time On Stream (Hr) | Phenol | Mono-Alkylate | 2,6- | Other Di-alkylate | 2,4,6- | Other Tri-alkylate |
| 5 | 3:1 | 500 | 250 | .5 | 22 | .6 | 4.2 | 16.9 | 12.2 | 44.8 | 17.6 |
| | | | 225 | | 44 | 2.1 | 6.7 | 28.7 | 8.7 | 41.9 | 13.1 |
| | | | 200 | | 66 | 3.1 | 10.1 | 37.8 | 7.4 | 31.7 | 7.0 |
| | | | 250 | | 88 | 1.0 | 5.9 | 22.1 | 13.4 | 44.7 | 11.0 |
| | | | 275 | | 114 | .9 | 5.8 | 17.8 | 18.8 | 42.6 | 12.1 |
| | | | 300 | | 138 | 1.1 | 6.9 | 11.0 | 31.3 | 32.9 | 14.7 |
| 6 | 37:63 | 750 | 250 | .5 | 28 | — | TRACE | 14.6 | 5.9 | 59.3 | 16.9 |
| | | | 225 | | 68 | — | .5 | 20.4 | 5.5 | 55.2 | 15.2 |
| | | | 250 | | 114 | — | TRACE | 11.9 | 5.7 | 59.2 | 19.7 |
| 7 | 1:1 | 500 | 250 | .5 | 132 | — | — | 5.3 | 10.6 | 60.2 | 18.3 |
| | | | | | 150 | — | — | 5.2 | 9.1 | 62.1 | 18.2 |
| | | | | | 188 | — | — | 7.4 | 10.8 | 59.6 | 17.9 |
| | | | 225 | | 224 | — | 2.9 | 19.5 | 11.6 | 53.2 | 11.5 |
| | | | | | 242 | .9 | 4.8 | 19.5 | 11.0 | 51.6 | 10.7 |

[a]Given as the Si/Al ratio.
[b]See note b of Table 1.

As is the case with batch isopropylation in an autoclave, the percent 2,4,6-triisopropylphenol peaks with usage of 1:1 silica-alumina.

What is claimed is:

1. A method of preparing 2,4,6-tri-sec-alkylphenol comprising reacting phenol with a monosubstituted or alpha, beta-disubstituted olefin at a temperature from about 150° to about 300° C. in the presence of a catalyst which is a composite consisting essentially of silica and alumina containing from about 40 to about 60% silica and from about 60 to about 40% alumina, and recovering the 2,4,6-tri-sec-alkylphenol.

2. The method of claim 1 where the olefin contains up to about 10 carbon atoms.

3. The method of claim 2 where the olefin is propylene and the product is 2,4,6-triisopropylphenol.

4. The method of claim 1 where the temperature is from about 200° to about 250° C.

5. The method of claim 2 where the composite is a synthetic silica-alumina.

6. The method of claim 5 where the composite contains about 50% silica and about 50% alumina.

* * * * *